United States Patent [19]

Luong et al.

[11] Patent Number: 5,288,613

[45] Date of Patent: Feb. 22, 1994

[54] ENZYME-BASED BIOSENSOR SYSTEM FOR MONITORING THE FRESHNESS OF FISH

[75] Inventors: John H. T. Luong, Mont-Royal; Keith B. Male, Verdun; An L. Nguyen, Dollard des Oremeaux, all of Canada

[73] Assignee: Her Majesty the Queen in right of Canada, as represented by the National Research Council of Canada, Ottawa, Canada

[21] Appl. No.: 802,698

[22] Filed: Dec. 5, 1991

Related U.S. Application Data

[63] Continuation of Ser. No. 563,116, Aug. 6, 1990, abandoned, which is a continuation-in-part of Ser. No. 157,390, Feb. 17, 1988, abandoned.

[51] Int. Cl.$^5$ .............. C12Q 1/26; C12Q 1/64; C12M 1/40; G01N 27/26
[52] U.S. Cl. .............................. 435/25; 435/9; 435/288; 435/817; 204/403
[58] Field of Search ............. 435/9, 288, 817, 25; 204/403

[56] References Cited

U.S. PATENT DOCUMENTS

| | | | |
|---|---|---|---|
| 4,581,336 | 4/1986 | Malloy et al. | 435/176 |
| 4,650,752 | 3/1987 | Ohashi et al. | 435/15 |
| 4,659,665 | 4/1987 | Freeman et al. | 435/182 |
| 4,713,165 | 12/1987 | Conover | 204/403 |

FOREIGN PATENT DOCUMENTS 58-005642  1/1983  Japan .
60-152947  8/1985  Japan .

OTHER PUBLICATIONS

Karube et al (1984) Determination of Fish Freshness with an Enzyme Sensor System. Agric. Food Chem 32:314-319.
Preston et al. (Jun. 1988) Novel Approach for Modifying Microporous Filters for Virus Concentration . . . Appl. Env. Micro. 54:1325-1329.
Luong et al. (May 1989) Appl. of Polarography for Monitoring the Fish Postmortem Metabolite Transformation for Enz. Microb. Tech. 11:277-282.
Mulchandani et al. (March 1990) Development of a Biosensor for Assaying Postmortem Nucleotide Degradation in Fish Tissues Biotech Bioeng 35:739-745.
Yutaka Fujii et al, "Relation between the Quality of Canned Fish and its Content of ATP-Breakdown-III. ATP-Breakdowns in Canned Albacore and Skipjack in Relation to the Organoleptic Inspection," Bulletin of the Japanese Society of Scientific Fisheries, 39(1), pp. 69-84 (1973).

(List continued on next page.)

Primary Examiner—Michael G. Wityshyn
Assistant Examiner—Ralph Gitomer
Attorney, Agent, or Firm—Shlesinger, Arkwright & Garvey

[57] ABSTRACT

The present invention relates to a method for determining the degree of freshness of raw, frozen and processed edible fish by monitoring the degradation of adenine triphosphate to inosine monophosphate, inosine and hypoxanthine. This method comprises simultaneously determining, by use of a suitable amperometric electrode such as platinum vs. silver/silver chloride polarized at 0.7 V, the amount of uric acid and hydrogen peroxide resulting from the degradation of hypoxanthine by xanthine oxidase, the degradation of inosine by the combined action of nucleoside phosphorylase and xanthine oxidase and the degradation of inosine monophosphate by the combined action of nucleotidase, nucleoside phosphorylase and xanthine oxidase. Also within the scope of this invention is a method for the immobilization of nucleotidase on the walls of a polymeric tube such as polystyrene tube and the co-immobilization of nucleoside phosphorylase and xanthine oxidase on a porous polymeric membrane such as a nylon membrane.

14 Claims, 5 Drawing Sheets

OTHER PUBLICATIONS

Tsuneyuki Saito et al, "A New Method of Estimating the Freshness of Fish," Bulletin of the Japanese Society of Scientific Fisheries, vol. 24, No. 9, pp. 749–750 (1959).

Fumiaki Uda et al, "Colorimetric Method for Measuring K Value, An Index for Evaluating Freshness of Fish," Bull. Tokai Reg. Fish. Res. Lab., No. 111, pp. 55–62 (Aug., 1983).

Hitoshi Uchiyama et al, "Significance in Measuring Volatile Base and Trimethylamine Nitrogen and Nucleotides in Fish Muscle as Indices of Freshness of Fish," Bulletin of the Japanese Society of Scientific Fisheries, vol. 36, No. 2, pp. 177–187 (1970).

Textbook of Clinical Chemistry, pp. 124–127, 1986, N. W. Tietz, "Analytical Procedures and Instrumentation".

Analytical Chemistry, vol. 46, No. 12, pp. 1769–1772, Oct., 1974, M. Nanjo, et al., "Enzyme Electrode Sensing Oxygen for Uric Acid in Serum and Urine".

Freshness Meter KV-101, Oriental Electrical Co., Ltd. Intended Use of YSI Model 23A Glucose Analyser, pp. 3–5 Catalog page, Unknown.

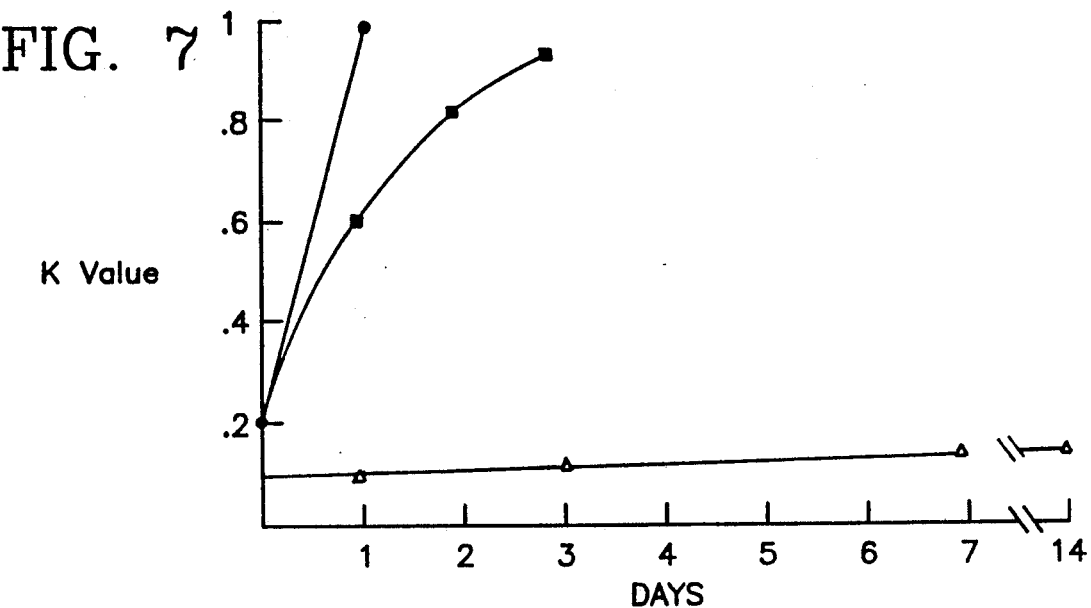
Time-course change of the K value at different storage temperatures
 (●) Room Temperature
 (■) 0-5°C
 (△) -20°C
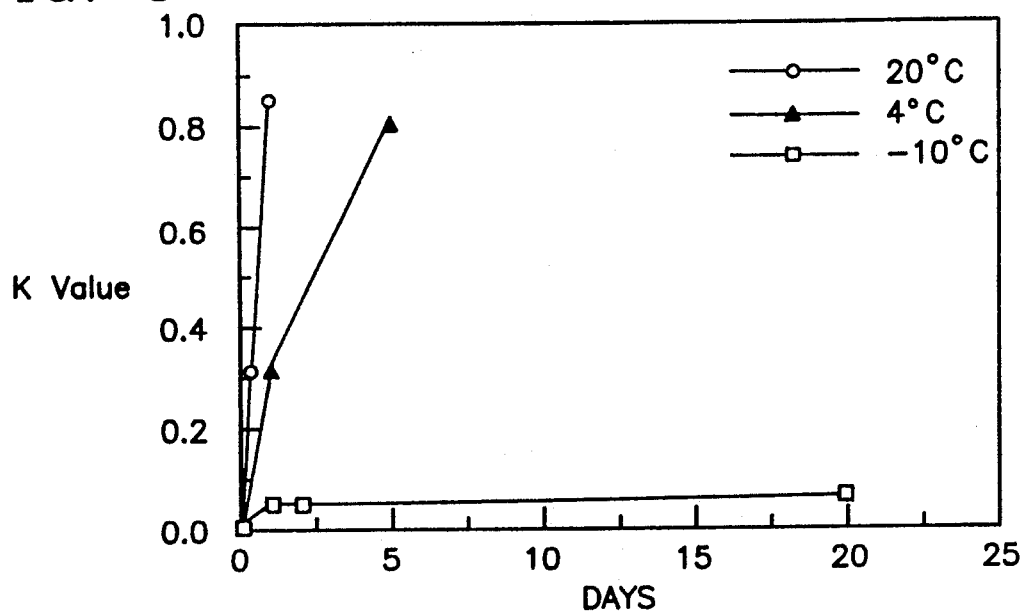

Comparison between K value of fish tissue extract samples determined with enzyme sensor system (ordinate) and conventional enzymatic method (abscissa):
(■)rainbow trout; (●)carp; (▲)haddock; (▼)sole.

ENZYME-BASED BIOSENSOR SYSTEM FOR MONITORING THE FRESHNESS OF FISH

This application is a continuation of application Ser. No. 07/563,116, filed on Aug. 6, 1990, now abandoned, which is a continuation in part of Ser. No. 07/157,390, filed Feb. 17, 1988, now abandoned.

BACKGROUND OF THE INVENTION

Fish and other types of marine organisms lose their freshness very rapidly after death. Furthermore, the quality of canned salmon, tuna, crab and the like is largely dependent upon the freshness of the fish or shellfish used for processing. Freshness of fish can rarely be visually determined because it is often sold in frozen or processed form.

From the standpoint of consumer protection and food hygiene, extensive research has been focused on the development of reliable and inexpensive methods of determination of fish freshness. This is urgently required in food industries since fish freshness is an important factor in the preparation of high-quality products. Indicators of fish freshness such as ammonia, amines, volatile acids, catalase activity, trimethylamine (TMA) and nucleotides have so far been proposed. Among these chemicals, nucleotides produced by adenosine triphosphate (ATP) decomposition are considered the most reliable and useful indicators. In recent years, considerable attention has been focused on nucleotide degradation in fish muscle as a reliable indicator of the freshness of raw fish.

Immediately after death, ATP in fish muscles is autolytically degraded to hypoxanthine/xanthine through the following autolytic pathway:

$$ATP \rightarrow ADP \rightarrow AMP \rightarrow IMP \rightarrow HxR \rightarrow Hx \rightarrow X \quad (1)$$

wherein
ATP is adenosine triphosphate
ADP is adenosine diphosphate
AMP is adenosine monophosphate
IMP is inosine monophosphate
HxR is inosine
Hx is hypoxanthine
X is xanthine.

Whereas IMP is one of the major contributing factors to the pleasant flavor of fresh fish, the accumulation of Hx and/or X during the storage results in an "off-taste". Several researchers have recognized that simultaneous determination of each nucleotide is necessary for a rapid estimation of freshness. From these observations, the concept of the K value was developed, in which:

$$K = \frac{[HxR] + [Hx]}{[ATP] + [ADP] + [AMP] + [IMP] + [Hx] + [HxR]} \quad (2)$$

In several fish species, however, ATP and ADP concentrations rapidly decrease and are negligible within 24 hours after death. Similarly, a rapid decline of AMP is also observed and its concentration is somewhat less than 1 μmol/g. In contrast to such behavior, IMP increases in the period ranging between 5 and 25 hours after death and then gradually decreases while the concentrations of HxR and Hx increase proportionally. In practice, the first measurements of fish freshness are usually performed at least 24 hours after death, thereby simplifying the determination of the K value in the following manner:

$$K = \frac{[HxR] + [Hx]}{[IMP] + [HxR] + [Hx]} \quad (3)$$

A low K value should be expected for fresh fish. It is generally believed that fish having a K value of less than 0.2 has excellent freshness qualities while fish exhibiting a K value ranging between 0.2 and 0.4 has good freshness qualities. The increase in the rate of the K value depends on the type of fish since changes in the K value are based on the enzymatic reactions within the fish meat. The K value also varies appreciably with temperature even among the same fish species.

Based on these facts, various freshness determination methods have been developed. For example, Uchiyama et al. (Bulletin of the Japanese Society of Scientific Fisheries, Vol. 36, 977 (1970)) made an analysis of the various nucleotides found in fish muscle by using liquid chromatography to show that a deterioration in freshness can be detected from an increase in the K value.

$$K = \frac{[HxR] + [Hx]}{[ATP] + [ADP] + [AMP] + [IMP] + [HxR] + [Hx]} \times 100\% \quad (4)$$

It was later determined by Nunata et al. in Journal of Japanese Society of Food Science and Technology, Vol. 28, 542 (1981) and by Kitada et al. in Journal of Japanese Society of Food Science and Technology, Vol. 30, No. 3, 151-154 (1983), that this method could also be used to determine the degree of freshness of poultry such as chicken.

However, the Uchiyama method has serious drawbacks, namely the necessity to use expensive liquid chromatography equipment that must be operated by skilled technicians, the time consuming separation and column regeneration as well as the difficulty in separating inosine from hypoxanthine.

Fujii et al. (Bulletin of the Japanese Society of Scientific Fisheries, Vol. 39, 69-84 (1973)) developed a method to estimate fish freshness based on the determination of the concentrations of IMP, HxR and Hx through enzymatic reactions. This method is based on the following equations:

$$IMP \text{ ratio} = \frac{[IMP]}{[IMP + HxR + Hx]} \times 100\% \quad (5)$$

$$HxR \text{ ratio} = \frac{[HxR]}{[IMP + HxR + Hx]} \times 100\% \quad (6)$$

$$Hx \text{ ratio} = \frac{[Hx]}{[IMP + HxR + Hx]} \times 100\% \quad (7)$$

The IMP ratio has a high value when the degree of freshness is high and decreases as the degree of freshness decreases. For example, canned tuna having an IMP ratio of 40% or higher can be judged as having been processed from raw tuna having a high degree of freshness.

Unfortunately, this method also presents serious drawbacks. Hence, an expensive ultraviolet spectrophotometer must be used to conduct certain measurements and two expensive enzymes are necessary in order to conduct a blank measurement and this enzymatic reaction is time consuming. Furthermore, corrosive perchloric acid must be used as the extractant since the ultraviolet absorbing properties of trichloroacetic acid render the latter unsuitable for use as the extractant.

The determination of the K value by monitoring oxygen consumption using a Clark oxygen electrode has been commercially exploited by Oriental Electric Co. Ltd. The apparatus is known as the KV-101 freshness meter (hereinafter referred to as the K-meter) and comprises a Clark oxygen electrode attached to a reaction chamber.

A major drawback of this technique is the low sensitivity and the requirement of a rigid control of pH and oxygen tension. In addition, the K-meter uses soluble enzymes which cannot be reused and there is a gradual loss of the probe's sensitivity, presumably due to the fowling of the electrode by the enzymes and/or compounds in fish extract. Other techniques of fish freshness determination have also been developed in recent years.

Karube et al. (J. Agric. Food Chem. 32, 314–319, 1984) described an enzyme sensor system for the determination of the K value. The system combined a double membrane consisting of a 5'-nucleotidase membrane and a nucleoside phosphorylase-xanthine oxidase membrane with an oxygen electrode. A small anion-exchange resin column was also connected with the enzyme sensor for separation of nucleotides. This biosensor system is less desirable for practical application since the three compounds in the mixture (IMP, HxR and Hx) had to be separated by an elaborate scheme using four different buffers and an anion exchange column, amounting to a very complicated procedure.

Ohashi et al. (U.S. Pat. No. 4,650,752) disclosed an enzymatic method for determining the K-value for fish and molluscs using soluble enzymes together with an oxygen electrode. The enzymes used for determining inosine and hypoxanthine concentrations are nucleoside phosphorylase and xanthine oxidase. To determine the concentration of the decomposition products of adenosine triphosphate, the enzymes alkaline phosphatase, adenylic acid kinase, AMP deaminase and adenosine deaminase in a crude extract obtained from calf intestine as well as nucleoside phosphorylase and xanthine oxidase are used. Again, the main drawback of this technique is the low sensitivity, the requirement of several enzymes and the costly enzymes that cannot be reused. Although Ohashi et al. state that the measurement can be determined electrochemically from the amount of hydrogen peroxide produced, no experimental data were presented to substantiate this statement.

Therefore, an inexpensive and rapid method useful in monitoring fish freshness would be highly desirable.

SUMMARY OF THE INVENTION

In accordance with the present invention, there is provided a method for determining the degree of freshness of raw, frozen and processed edible fish by monitoring the degradation of adenine triphosphate to inosine monophosphate, inosine and hypoxanthine. The method comprises firstly extracting edible fish with a solution of an acid useful to break cell membranes such as trichloroacetic acid, in order to produce an extract. A first portion of this extract is contacted with the enzymes xanthine oxidase and nucleoside phosphorylase and a value $d_1$ is electrochemically measured through a single electrode from the simultaneous determination of the amount of hydrogen peroxide and uric acid resulting from the degradation of hypoxanthine and inosine by these two enzymes.

This is followed by contacting a second portion of the fish extract with the enzymes xanthine oxidase, nucleoside phosphorylase and nucleotidase and electrochemically measuring through a single electrode a value $d_2$ from the simultaneous determination of the amount of hydrogen peroxide and uric acid resulting from the degradation of inosine monophosphate, inosine and hypoxanthine by these three enzymes.

Based on values $d_1$ and $d_2$, the index of freshness is determined from the formula $K=d_1/d_2$ where K represents the index of freshness, $d_1$ represents the combined concentrations of inosine and hypoxanthine and $d_2$ represents the combined concentrations of inosine monophosphate, inosine and hypoxanthine.

It has been discovered that the simultaneous determination of both the amount of uric acid and hydrogen peroxide may be achieved through the use of an amperometric electrode polarized at $+0.7$ V. The simultaneous determination of both uric acid and hydrogen peroxide concentrations enables accurate measurements of both values $d_1$ and $d_2$ and thus accurate determination of the index of freshness. Preferably, the electrode to be used is a platinum vs. silver/silver chloride electrode polarized at $+0.7$ V.

A preferred embodiment of the process of the present invention consists in co-immobilizing the enzymes xanthine oxidase and nucleoside phosphorylase on a porous polymeric membrane, more preferably a nylon membrane.

The immobilization of the enzymes on porous membranes is advantageous since it enables the enzymes to be used several times, thereby substantially simplifying the method and reducing its costs.

Also within the scope of the present invention is a method for the preparation of the immobilized enzymes used in the freshness determination of edible fish that is: xanthine oxidase, nucleoside phosphorylase, and nucleotidase. The method comprises immobilizing a first enzyme, such as nucleotidase, on a polymeric support. The immobilization is accomplished by contacting this support with a polyethyleneimine solution, a solution containing a crosslinking agent and a solution containing the enzyme to be immobilized. A second and a third enzyme, such as xanthine oxidase and nucleoside phosphorylase, are also immobilized on a porous polymeric membrane by contacting this membrane with a solution comprising the enzymes and a crosslinking agent. Preferably, the enzymes xanthine oxidase and nucleoside phosphorylase are co-immobilized on a porous nylon membrane or the like and nucleotidase is immobilized via glutaraldehyde activation on the wall of a polymeric tube such as a polystyrene tube precoated with a thin layer of polyethyleneimine.

The term "edible fish", when used herein, is intended to include a variety of marine organisms comprising various fish species such as salmon, sole and trout as well as crab meat, lobster and the like.

IN THE DRAWINGS

FIG. 7 represents the time course change of the K value of trout at different storage temperatures.

FIG. 8 represents the time course change of the K value of lobster at different storage temperatures.

DETAILED DESCRIPTION OF THE INVENTION

Figure 1:
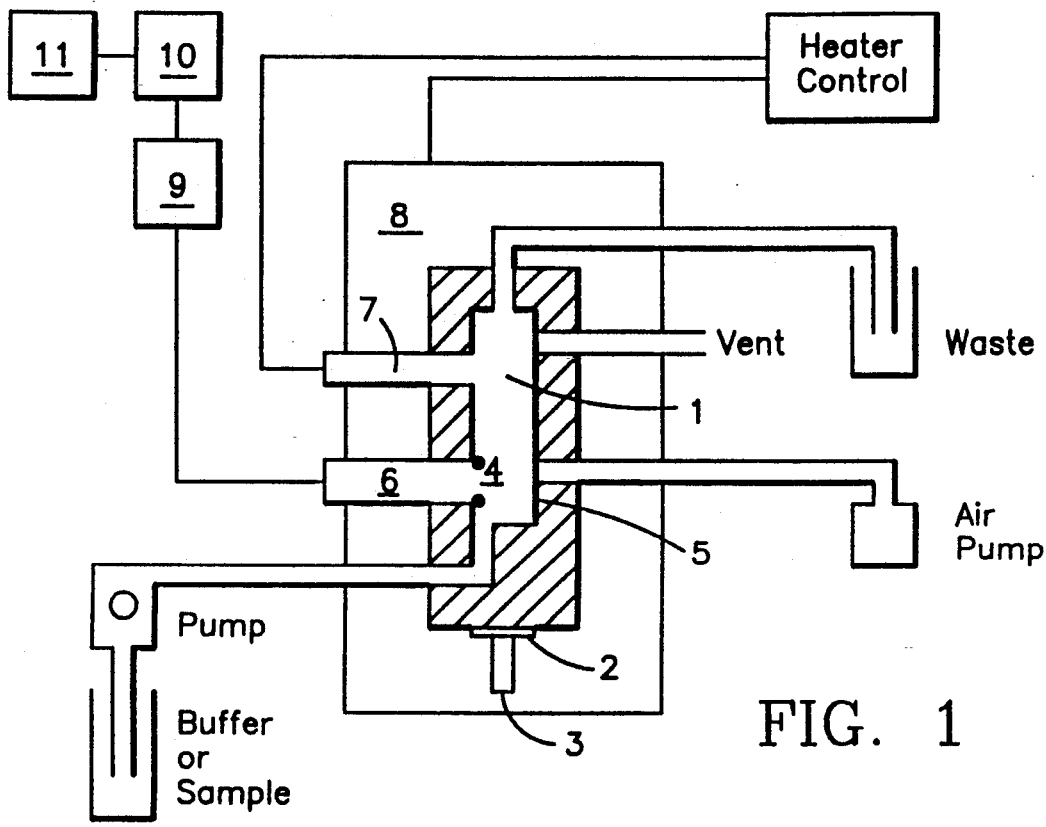
FIG. 1 is a diagram of the apparatus used in the context of the present invention.

The present invention is concerned with a new method useful in monitoring the freshness of various edible fish by the determination of their respective K value. The determination of the K value is obtained by using an amperometric electrode which can detect the presence of both hydrogen peroxide and uric acid. For example, after the death of many fish species, inosine monophosphate (IMP) contained in their muscle is degraded in the following manner:

  (8)

  (9)

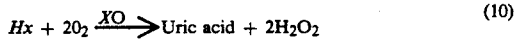  (10)

wherein NT, NP, XO and $P_i$ are nucleotidase, nucleoside phosphorylase, xanthine oxidase, and inorganic phosphate, respectively.

As demonstrated above, each mole of inosine monophosphate consumed will ultimately require two moles of oxygen and liberate two moles of hydrogen peroxide as well as one mole of uric acid. It is therefore inosine, or inosine monophosphate by following either the rate of oxygen consumption or the rate of hydrogen peroxide formation. As mentioned above, the monitoring of oxygen consumption presents serious drawbacks.

Amperometric detection of enzymatically generated hydrogen peroxide has been widely performed by using a Clark hydrogen peroxide electrode (referred to hereinafter as the amperometric electrode). Basically, this electrode consists of a platinum anode and a silver/silver chloride cathode where the anode is polarized at 0.5 V to +0.7 V with respect to the cathode. The amperometric probe oxidizes a constant portion of the hydrogen peroxide at the platinum anode at such a polarized potential.

  (11)

The current thus created is directly proportional to the hydrogen peroxide level formed during the oxidation of Hx to uric acid by the enzyme xanthine oxidase as shown in equation 10. However it should be noted that various reducing substances such as ascorbic acid, glutathione, uric acid, etc., may considerably influence the oxidation of $H_2O_2$. Consequently, there is a problem for determining the level of $H_2O_2$ formed during the oxidation of Hx since the amperometric electrode will respond to both $H_2O_2$ and uric acid. As experimentally confirmed by Nanjo and Guilbault in Anal. Chem. 46, 1769 (1974), uric acid is electroactive and provides a limiting current at the same potential (0.5 V to +0.7 V) where hydrogen peroxide is oxidized. The electrochemical oxidation of uric acid can be described by the following reaction.

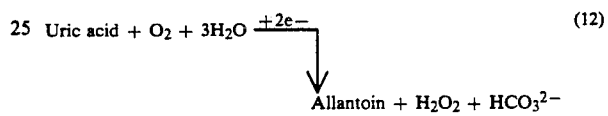  (12)

Any attempt to separate the currents by pH variations is not advisable since the current-potential (i-E) curves of uric acid and hydrogen peroxide behave similarly with changes in pH.

In the present invention, it has been discovered that the amperometric electrode responds to a sample containing both uric acid and hydrogen peroxide in an additive manner.

The [Hx+HxR] concentration in tissue extract can therefore be measured by using nucleoside phosphorylase and xanthine oxidase which are preferably co-immobilized on a porous polymeric membrane. Various types of porous polymeric materials such as cellulose, nylon and the like may be used in the context of the present invention, although nylon appears to be the most preferred one. The shape, size and thickness of this membrane do not seem to be critical to the viability of the process. In fact, what is needed is a porous polymer suitable to immobilize one or more enzymes. The electrode amperometrically detects the products of the enzymatic degradation of Hx and HxR, hydrogen peroxide and uric acid.

For the determination of [IMP+HxR+Hx], IMP is first converted to HxR by nucleotidase. Preferably, the enzyme is to be immobilized on the walls of a polymeric tube, precoated with a thin layer of polyethyleneimine. Again, the nature of the polymeric material is not critical but polymers such as polystyrene and the like should be employed. The [IMP+Hx+HxR] concentration is then measured by the aforementioned electrode.

Referring now to the drawings, FIG. 1 shows an example of the instrument used in the present invention. In FIG. 1, the sample measurement chamber 1, the volume of which is preferably ranging from 0.3 to 0.4 ml, comprises a stopper 2 provided with a capillary 3 used for liquid injection in the center thereof, said capillary having, for example, a diameter of about 0.125 mm. The sample measurement chamber 1 is hermetically sealed by a ring 4 and the samples contained in the measurement chamber 1 are stirred by an air driven silicon diaphragm 5 which is used to provide both adequate mixing of the solution and abundant supply of oxygen to support the reaction. The reaction chamber 1 also contains an amperometric electrode 6 on which is affixed a porous polymeric membrane on which the nucleoside phosphorylase and xanthine oxidase enzymes have previously been immobilized. The amperometric electrode consists of a platinum anode polarized at +0.7 V versus a silver/silver chloride cathode. Both the electrode 6 and a temperature probe 7 are mounted in the sample measurement chamber 1. The sample measurement chamber 1 is surrounded by a block heater 8 used to provide adequate temperature control.

Description of a Preferred Embodiment Using Immobilized Enzymes for the Determination of Fish Freshness Materials and Methods a) Immobilization of Nucleotidase on the Wall of a Polystyrene Tube.

Nucleotidase (NT) was immobilized on the wall of a 1-mL polystyrene centrifuge tube. The tube was filled with 1 mL of 5% polyethyleneimine solution and incubated at room temperature (20°-24° C.) for 2 h. The tube was then emptied and filled with 2.5% of a crosslinking agent solution such as a glutaraldehyde solution in 150 mM, pH 7.8, phosphate buffer. Incubation was carried out at room temperature for 3 h. Glutaraldehyde solution was then removed and the tube was washed thoroughly with 150 mM, pH 7.8, phosphate buffer. The tube was filled with 1 mL solution containing 5-6 IU of nucleotidase dissolved in 4 mM, pH 7.8, phosphate buffer and incubated overnight at 4° C. The solution was then removed and the tube was washed extensively with the buffer and stored filled with buffer at 4° C.

b) Co-immobilization of Nucleoside Phosphorylase and Xanthine Oxidase on a Membrane.

A prewetted Immunodyne ™ membrane (1.5×1.5 cm) was stretched on the tip of a hollow plastic cylinder (1 cm diameter) and held in place by an O-ring. The preactivated Immunodyne ™ nylon 66 membrane (pore size of 3μm) was obtained from Pall BioSupport Division (Glen Cove, N.Y.). The membrane is intrinsically hydrophilic and contains function groups which form covalent linkages with a variety of nucleophilic groups of enzymes/proteins.

To a mixture containing 20 μl of nucleoside phosphorylase (NP, 5.1 g/l and 3.6 U/mg), 4 μl of bovine serum albumin (BSA, 400 g/l), and 18 μl of buffer (200 mM) pH 7 phosphate), 8 μof glutaraldehyde (12.5% w/v) was added to initiate the crosslinking. It should be noted that the final volume of the resulting solution is 50 μl and contained 2% w/v glutaraldehyde, 1.6 mg BSA and 102 μg NP. 35 μl of the resulting solution was then layered on the prewetted membrane and the solution was allowed to crosslink at room temperature (20°-24° C.) until a yellowish hard gel layer was obtained (20-30 min). The membrane was then removed and washed extensively with phosphate buffer (50 mM, pH 7.8) to remove unreacted glutaraldehyde. The final concentration of NP and BSA was thus estimated to be 71 μg and 1.12 mg, respectively. It should be noted that the resulting NP activity increased with glutaraldehyde concentration used and reached maximum at 1% (w/v).

Figure 2:
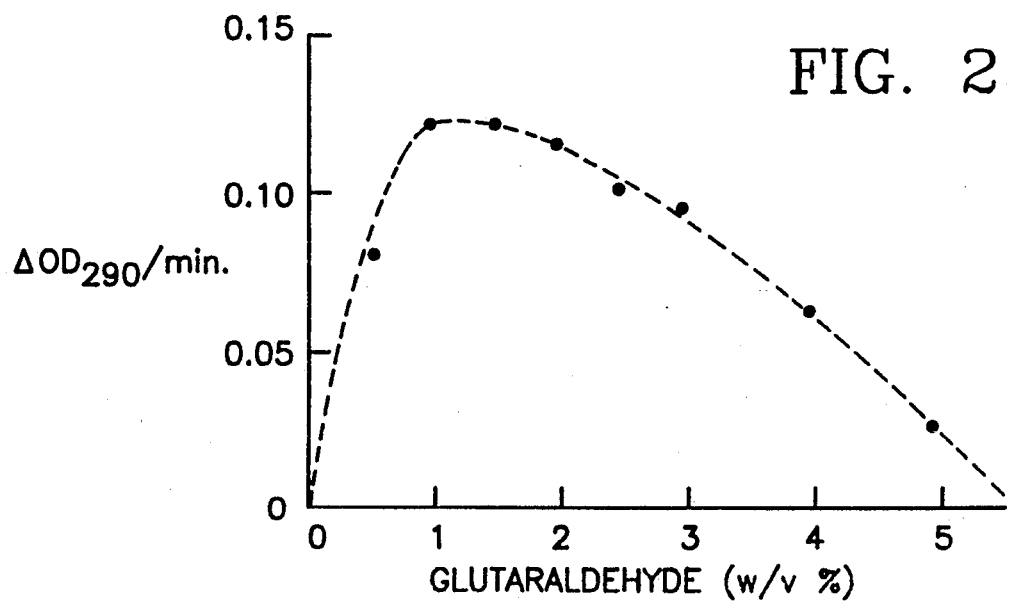
FIG. 2 represents the effect of glutaraldehyde concentration on the activity of the immobilized enzyme (measured as $\Delta OD_{290}/min$; $OD_{290}=$optical density or absorbance at 290 nm) by following uric acid produced from inosine by the action of nucleoside phosphorylase and xanthine oxidase immobilized on the membrane.

The membranes prepared with glutaraldehyde concentrations below 1% exhibited a very soft layer which was easily damaged/detached. Increase in glutaraldehyde concentration beyond 1% (w/v) resulted in decreased NP activity as shown in FIG. 2. The NP activity decreased drastically at glutaraldehyde concentrations above 2%. However, the enzyme layer obtained under such a condition was much stronger and slightly yellow.

Apparently, a low glutaraldehyde concentration resulted in an insufficient protein crosslinking and led to washing away of the enzyme. On the other hand, at a high glutaraldehyde level, the enzyme and BSA were extensively crosslinked to form a thick gel which causes severe diffusional limitation and destruction of the enzyme active sites. A concentration of 2% glutaraldehyde was considered optimal since it represents a good compromise between the enzyme activity and the mechanical strength of the enzyme layer.

Figure 3:
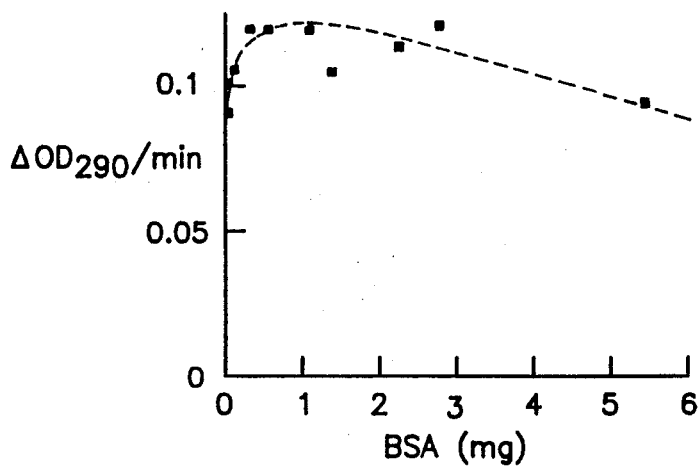
FIG. 3 illustrates the effect of the amount of bovine serum albumin on the activity (measured as $\Delta OD_{290}/min$) of nucleoside phosphorylase immobilized on the membrane.

To a lesser extent, the activity of NP in the enzyme layer was also affected by BSA concentration as shown in FIG. 3. The enzyme activity increased slightly with albumin concentration, reached a maximum, and then decreased. The decrease in the activity can be attributed to an increased diffusional resistance of the complex matrix. Once again, at a low albumin concentration, the enzyme layer formed was not firm and easily damaged/detached. At a higher albumin concentration, the layer was hard and yellow. As a result of this finding, 1.12 mg of albumin was considered optimum.

Figure 4:
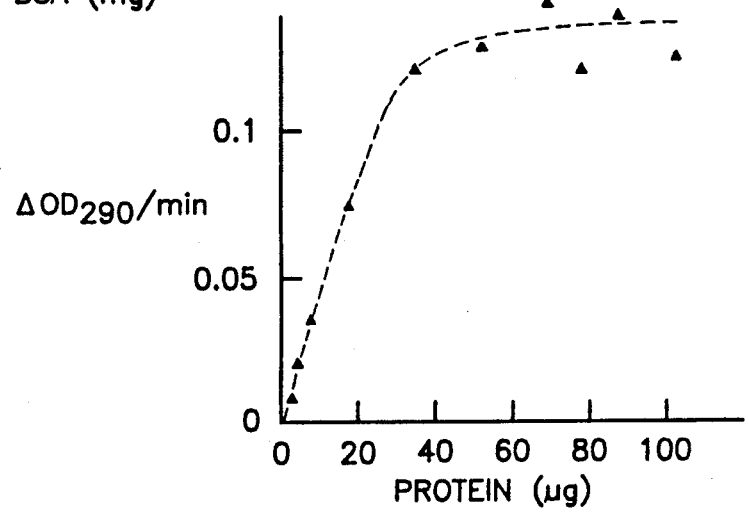
FIG. 4 represents the relationship between the amount of protein (specific activity of nucleoside phosphorylase 36 IU/mg protein) and the activity (measured as $\Delta OD_{290}/min$) of immobilized enzyme.

As expected, the activity of the immobilized NP was dependent on the amount of enzyme used for membrane preparation as shown in FIG. 4. Below 20 μg NP, there was a linear relationship between the activity of the immobilized enzyme and the amount of enzyme used. Beyond 70 μg NP, the activity of the enzyme membrane was independent of any further increase in the enzyme concentration used during immobilization. Consequently, 2.6 IU or 71 μg NP was used for enzyme layer preparation.

After NP was immobilized, the membrane was washed extensively with 50 mM phosphate buffer and it was then immersed in a centrifuge tube containing 2 mL of 25 mM, pH 7.5, tris buffer and 0.27 IU xanthine oxidase (XO). The tube was continuously agitated on a vortex mixer (model 5432, Eppendorf Gerätebau, Hamburg, FRG) for 4 h. at 4° C. The membrane was then washed several times with cold phosphate buffer (50 mM, pH 7.8, 4° C.) to remove unbound xanthine oxidase. A circular disk of the size matching with the electrode was cut out of the membrane loaded with enzymes (henceforth referred as enzymic membrane) and stored at 4° C. in the same buffer containing 1.0 mM $Mg^{2+}$.

Effect of pH on the Activity of Immobilized Enzymes

Figure 5:
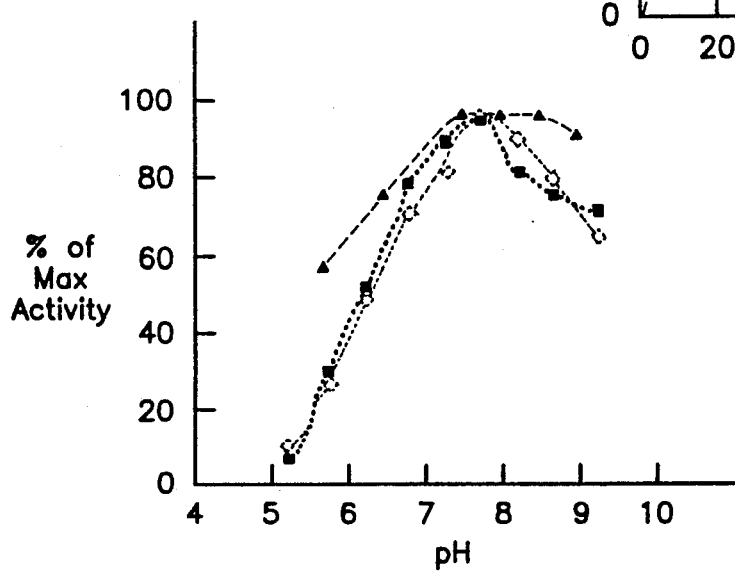
FIG. 5 represents the activity vs. pH profile of immobilized enzymes: (▲) nucleotidase; and immobilized xanthine oxidase and nucleoside phosphorylase for (◇) hypoxanthine and (♦) inosine as substrate.

The effect of pH on the activity of the resulting enzymic membrane is illustrated in FIG. 5. The enzyme xanthine oxidase exhibited a maximum activity at pH 7.8 when hypoxanthine was used as substrate. Similarly, for the inosine substrate, the pH optimum for both xanthine oxidase and nucleoside phosphorylase was also about 7.8. The immobilized enzyme nucleotidase exhibited a broad optimum pH (7.5 to 9). Therefore, pH 7.8 was recommended for analysis using the newly developed enzyme sensor system in this invention.

Response of the Biosensor System to Samples Containing HxR or Hx

Figure 6A:
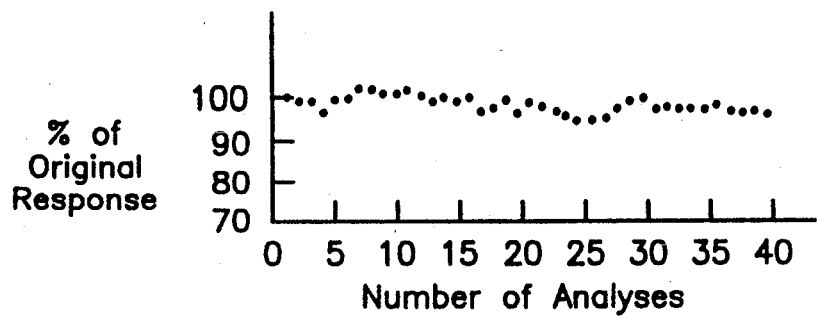
FIG. 6A illustrates the reproducability of analyses for fish extract (A) Hx with immobilized NP and XO membrane.
Figure 6B:
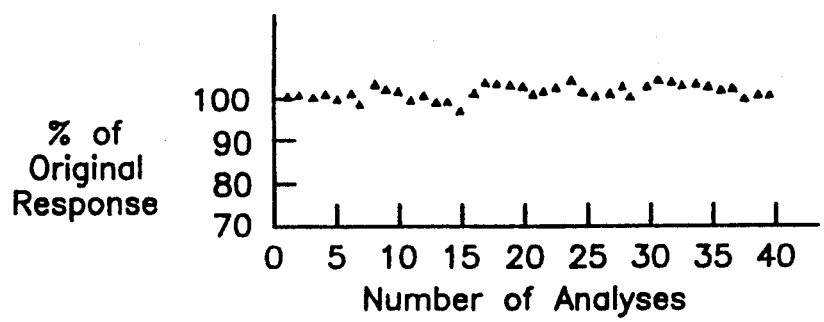
FIG. 6B illustrates the reproducibility of analyses for fish extract (B) HxR with immobilized NP and XO membrane.
Figure 6C:
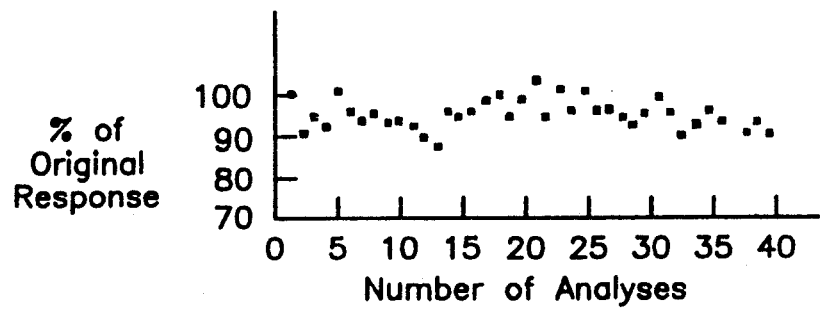
FIG. 6C illustrates the reproducability of analyses for fish extract (C) IMP with immobilized NT tube.
Figure 9:
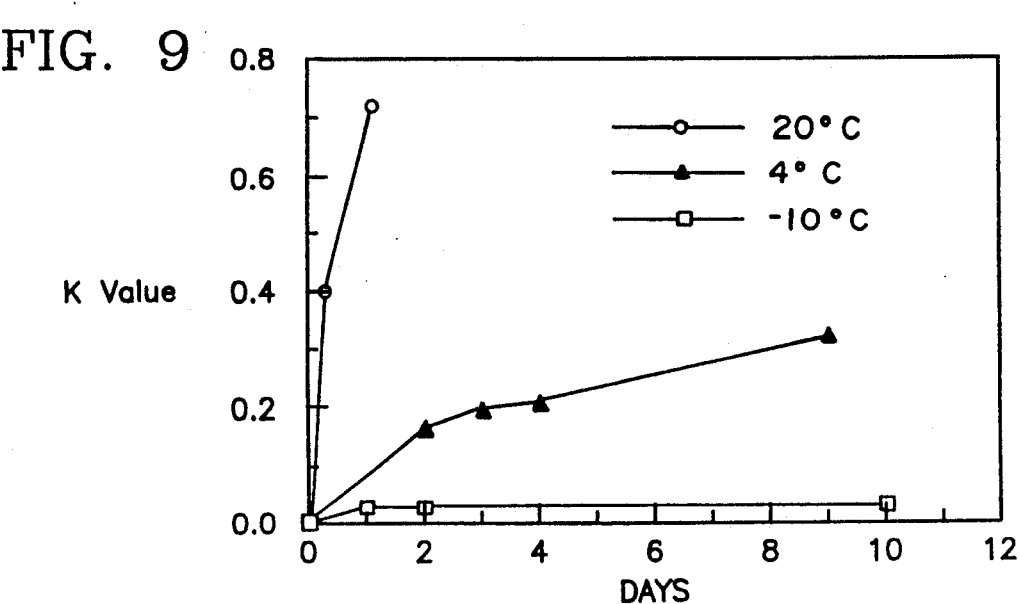
FIG. 9 represents the time course change of the K value of shrimp at different storage temperatures.

An excellent linear relation existed between the electrode output and HxR concentration up to 143 μM. The slope was determined to be 11.3 mV μM$^{-1}$ with a correlation coefficient of 1 (standard deviation of ±4.8). The minimum detectable concentration of HxR was determined to be 3.6 μM. The reproducibility was ±4% for repeated analyses of 7.14 μM of HxR as illustrated in FIG. 6B. The standard deviation for 40 repeated assays was ±0.14 μM. Similarly, a good reproducibility (±3%) (FIG. 6A) and a low standard deviation (±0.13 μM) were observed when 7.14 μM Hx was assayed repeatedly. The membranes were stable at least up to two months with respect to NP activity when stored at 4° C. in 50 mM, pH 7.8, phosphate buffer containing 1 mM magnesium. Under similar conditions, there was a 20% decrease in XO activity. However, this activity loss did not affect the membrane performance when used in the analyzer. The response to HxR was approximately 81 ±2% of an equimolar Hx sample and the membrane was useful for at least 40 repeated analyses. The enzyme electrode developed in this study monitored the products of degradation, hydrogen peroxide and uric acid, and exhibited a 125-fold higher sensitivity than the enzyme electrode based on oxygen detection. The higher sensitivity can be attributed to the detection of three moles of products released per mole of inosine consumed compared to the detection of two moles of oxygen consumed for each mole of inosine degraded and lower diffusional resistance of the nylon membrane.

Determination of the Freshness of Various Edible Fish

Tissue samples from fish fillet (ca. 2 g) were homogenized with about 10% trichloroacetic acid (4 ml) using a homogenizer. It has been found that a trichloroacetic acid concentration of about 10% was suitable for the purposes of the present invention although other acids and possible different concentrations could be contemplated. In fact, one needs an acid in sufficient concentration to break the cell membrane of the fish sample to be analyzed. The supernatant obtained after centrifugation at 27,000 g force was neutralized with 2M sodium hydroxide solution. The sample was then diluted up to 5 fold using 50 mM glycine+5 mM MgSO$_4$ buffer (pH 7.5). It should be noted that due to the highly acidic nature of the fish extract, it is somewhat difficult to adjust pH 7 to the desired value. Therefore, it was necessary to use a high ionic-strength buffer for assay of fish samples. However, it should be borne in mind that phosphate ions of high concentration resulted in a high background reading in the biosensor. Therefore, 50 mM glycine+5 mM MgSO$_4$, pH 7.5 buffer was used for fish sample analyses.

The numerator in Eq. (3) or [Hx+HxR] was determined by injecting 25 μl diluted extract in a reaction chamber equipped with the xanthine oxidase-nucleoside phosphorylase enzyme electrode described above. The output of the electrode increased and approached a plateau in 90-120 seconds ($d_1$). For [IMP+Hx+HxR] measurements, 500 μl of diluted extract was reacted with the immobilized nucleotidase for 5-10 min. under constant shaking on a vortex mixer and 25 μl of the resulting product was injected to the reaction chamber. The result recorded after 2 minutes ($d_2$) was used together with $d_1$ to calculate the K value $d_1/d_2$.

The process referred to above is also described in the publications entitled "Development and application of a biosensor for hypoxanthine in fish extract", *Analytica Chimica Acta*, 221 (1989), 215–222 and "Development of a biosensor for assaying postmortem nucleotide degradation in fish tissues", Biotechnology and Bioengineering, Vol. 35, pp. 739–734 (1990), which are hereby incorporated by reference.

Practical Considerations

In terms of cost effectiveness, the method of the present invention demonstrates several advantages. First, the method of the present invention offers a rapid, simple and accurate method for K value determination, the freshness indicator of edible fish meat. Secondly, the enzyme membrane consisting of nucleoside phosphorylase and xanthine oxidase provides excellent reproducible results for at least 40 repeated assays and immobilized nucleotidase is good for at least 40 assays as well. Furthermore, in addition to the low cost of analysis, apparati associated with sample handling and preparation as well as the reaction chamber equipped with an amperometric electrode are compact and suitable for field work.

The following examples are intended to illustrate rather than limit the scope of the present invention.

EXAMPLE 1

The procedure described under the heading "Determination of the freshness of various edible fish" was repeated on a tissue taken from a freshly caught rainbow trout. The K value was determined to be approximately 0.1.

EXAMPLE 2

The procedure described in Example 1 was repeated on a tissue sample taken from a rainbow trout 24 hours after death. The fish had been maintained at room temperature. The recorded K value was estimated to be approximately 1.

EXAMPLE 3

The procedure described in Example 1 was repeated on a tissue sample taken from a rainbow trout 24 hours after death. The fish had been maintained at a temperature ranging between 0° and 5° C. The K value was estimated to be 0.61.

EXAMPLE 4

The procedure described in Example 1 was repeated on a tissue sample taken from a rainbow trout 72 hours after death. The fish had been maintained at a temperature ranging between 0° and 5° C. The K value was determined to be 1.

EXAMPLE 5

The procedure described in Example 1 was repeated on a tissue sample taken from a rainbow trout 2 weeks after death. The fish had been maintained at a temperature of −20° C. The estimated K value was determined to be 0.15.

EXAMPLE 6

The procedure described in Example 1 was repeated using six samples taken from the muscle of frozen sole. The average K value was determined to be approximately 0.65.

EXAMPLE 7

The procedure described in Example 6 was repeated using a tissue sample taken from sole which had been maintained at −20° C. for 2 months. The estimated K value was determined to be 0.65.

EXAMPLE 8

The procedure described in Example 6 was repeated using a tissue sample taken from sole which had been maintained at 5° C. for 24 hours. The estimated K value was determined to be 1.

EXAMPLE 9

The procedure described in Example 6 was repeated using a tissue sample from the muscle of salmon frozen for 3 weeks after being caught. The K value was determined to be 0.37.

EXAMPLE 10

The procedure described in Example 9 was repeated on a tissue sample taken from the frozen salmon and maintained at room temperature for 24 hours. The recorded K value was estimated to be approximately 1.

EXAMPLE 11

The procedure described in Example 9 was repeated on a tissue sample taken from the frozen salmon and maintained at 0°–5° C. for 24 hours. The recorded K value was estimated to be approximately 0.76.

EXAMPLE 12

The procedure described in Example 9 was repeated on a tissue sample taken from the frozen salmon and maintained at 0°–5° C. for 48 hours. The recorded K value was estimated to be approximately 1.

EXAMPLE 13

The procedure described in Example 9 was repeated on a tissue sample taken from the frozen salmon and maintained at −20° C. for a further 2 weeks. The recorded K value was estimated to be approximately 0.75.

EXAMPLE 14

The procedure described in Example 1 was repeated on a tissue sample taken from the muscle of freshly caught carp. The K value was determined to be 0.31.

EXAMPLE 15

The procedure in Example 14 was repeated on a tissue sample taken from a carp 24 hours after death. The fish had been maintained at a temperature ranging between 0° and 5° C. The K value was estimated to be 0.78.

EXAMPLE 16

The procedure in Example 14 was repeated on a tissue sample taken from a carp 48 hours after death. The fish had been maintained at a temperature ranging between 0° and 5° C. The K value was estimated to be 1.

EXAMPLE 17

The procedure in Example 14 was repeated on a tissue sample taken from a carp 1 week after death. The fish had been maintained at a temperature of −20° C. The K value was estimated to be 0.29.

EXAMPLE 18

The procedure in Example 1 was repeated on a tissue sample taken from a live lobster. The estimated K value was very close to zero (0.03).

EXAMPLE 19

The procedure in Example 1 was repeated on a tissue sample taken from lobster 12 hours after death. The lobster had been maintained at a temperature of 20° C. The K value was estimated to be 0.24.

EXAMPLE 20

The procedure in Example 1 was repeated on a tissue sample taken from lobster 24 hours after death. The lobster had been maintained at a temperature of 20° C. The K value was estimated to be 0.94.

EXAMPLE 21

The procedure in Example 1 was repeated on a tissue sample taken from lobster 24 hours after death. The lobster had been maintained at a temperature of 4° C. The K value was estimated to be 0.24.

EXAMPLE 22

The procedure in Example 1 was repeated on a tissue sample taken from lobster 5 days after death. The lobster had been maintained at a temperature of 4° C. The K value was estimated to be 0.80.

EXAMPLE 23

The procedure in Example 1 was repeated on a tissue sample taken from lobster 24 hours after death. The lobster had been maintained at a temperature of −10° C. The K value was estimated to be 0.06.

EXAMPLE 24

The procedure in Example 1 was repeated on a tissue sample taken from lobster 2 days after death. The lobster had been maintained at a temperature of −10° C. The K value was estimated to be 0.06.

EXAMPLE 25

The procedure in Example 1 was repeated on a tissue sample taken from lobster 20 days after death. The lobster had been maintained at a temperature of −10° C. The K value was estimated to be 0.08.

EXAMPLE 26

The procedure in Example 1 was repeated on a tissue sample taken from a live shrimp. The K value was estimated to be close to zero.

EXAMPLE 27

The procedure in Example 1 was repeated on a tissue sample taken from shrimp 12 hours after death. The shrimp had been maintained at a temperature of 20° C. The K value was estimated to be 0.4.

EXAMPLE 28

The procedure in Example 1 was repeated on a tissue sample taken from shrimp 24 hours after death. The shrimp had been maintained at a temperature of 20° C. The K value was estimated to be 0.73.

EXAMPLE 29

The procedure in Example 1 was repeated on a tissue sample taken from shrimp 2 days after death. The shrimp had been maintained at a temperature of 4° C. The K value was estimated to be 0.15.

EXAMPLE 30

The procedure in Example 1 was repeated on a tissue sample taken from shrimp 3 days after death. The shrimp had been maintained at a temperature of 4° C. The K value was estimated to be 0.19.

EXAMPLE 31

The procedure in Example 1 was repeated on a tissue sample taken from shrimp 4 days after death. The shrimp had been maintained at a temperature of 4° C. The K value was estimated to be 0.2.

EXAMPLE 32

The procedure in Example 1 was repeated on a tissue sample taken from shrimp 9 days after death. The shrimp had been maintained at a temperature of 4° C. The K value was estimated to be 0.38.

EXAMPLE 33

The procedure in Example 1 was repeated on a tissue sample taken from shrimp 1 day after death. The shrimp had been maintained at a temperature of $-10°$ C. The K value was estimated to be 0.04.

EXAMPLE 34

The procedure in Example 1 was repeated on a tissue sample taken from shrimp 2 days after death. The shrimp had been maintained at a temperature of $-10°$ C. The K value was estimated to be 0.04.

EXAMPLE 35

The procedure in Example 1 was repeated on a tissue sample taken from shrimp 10 days after death. The shrimp had been maintained at a temperature of $-10°$ C. The K value was estimated to be 0.04.

c) Validity of the Results Obtained

Figure 10:
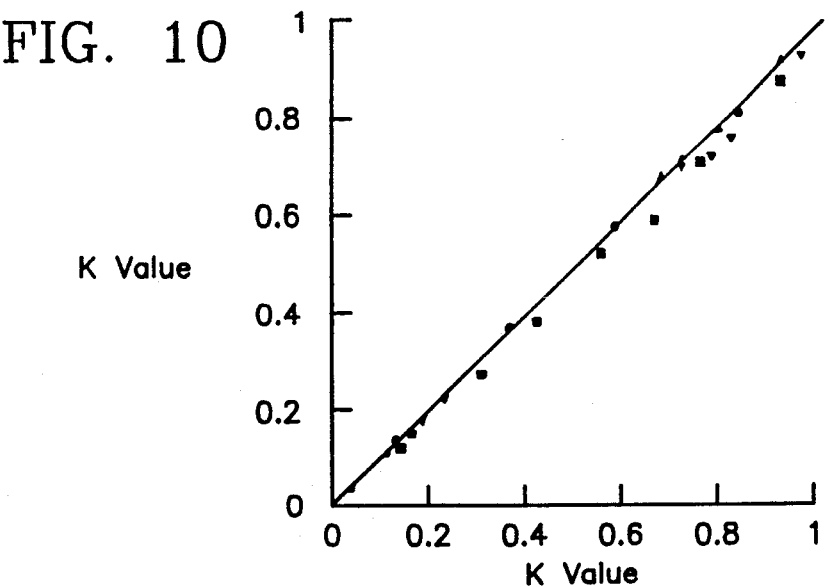
FIG. 10 represents a comparison between K values determined with the biosensor system and the conventional enzymatic method.

There was excellent agreement between the K value determined by the biosensor system developed in this invention and those determined by the conventional enzymatic assay as shown in FIG. 10. The slope was determined to be 0.967 with a correlation coefficient of 0.998 and a standard deviation of ±0.021.

For the conventional enzymatic assay, the extract prepared as described above was diluted up to 40-fold. To 1 mL of diluted extract in 10 mM, pH 7.8 phosphate buffer, 0.18 IU XO, 0.036 IU NP and 1.5 IU nucleotidase were added sequentially. The concentrations of Hx, HxR and IMP were determined, respectively from the three plateaus of uric acid produced according to equations (8-10). The K value was of course calculated according to Equation (3).

TABLE 1

Estimation of the K value of frozen sole fillet by the amperometric electrode

| Sample # | Dilution Factor | Amperometric electrode response | | K value |
|---|---|---|---|---|
| | | $d_1$ | $d_2$ | |
| 1 | 60× | 113 | 170 | 0.66 |
| | 30× | 235 | 355 | 0.66 |
| 2 | 60× | 130 | 175 | 0.74 |
| | 30× | 228 | 345 | 0.66 |
| 3 | 60× | 125 | 198 | 0.63 |
| | 30× | 233 | 355 | 0.66 |
| 4 | 60× | 105 | 150 | 0.70 |
| 5 | 30× | 200 | 280 | 0.71 |
| | 60× | 113 | 185 | 0.61 |
| | 30× | 223 | 360 | 0.62 |
| 6 | 30× | 258 | 353 | 0.73 |

This is a continuation-in-part of U.S. application Ser. No. 157,390 filed Feb. 17, 1988, which is hereby incorporated by reference.

We claim:

1. A method for determining the degree of freshness of raw, frozen or processed edible fish by monitoring the autolytic degradation of adenosine triphosphate in fish muscles to inosine monophosphate, inosine and hypoxanthine, said method comprising:
   (a) providing a homogenous fish muscle extract wherein the cell membrane of the fish muscle has been broken;
   (b) contacting a first portion of said extract with the enzymes xanthine oxidase and nucleoside phosphorylase and electrochemically measuring through an amperometric probe, comprising an anode and a cathode, a value $d_1 = [HxR] + [Hx]$ from the simultaneous determination of the amount of hydrogen peroxide and uric acid resulting from the degradation of hypoxanthine and inosine in said first extract portion by said enzymes, wherein [HxR] is the concentration of inosine and [Hx] is the concentration of hypoxanthine;
   (c) contacting a second portion of said extract with the enzymes nucleotidase, nucleoside phosphorylase and xanthine oxidase, and electrochemically measuring through an amperometric probe, comprising an anode and a cathode, a value $d_2 = [IMP] + [HxR] + [Hx]$ from the simultaneous determination of the amount of hydrogen peroxide and uric acid resulting from the degradation of inosine monophosphate, inosine and hypoxanthine in said second extract portion by said enzymes, wherein [IMP] is the concentration of inosine monophosphate, [HxR] is the concentration of inosine, and [Hx] is the concentration of hypoxanthine; and
   (d) determining the index of freshness from the formula $K = d_1/d_2$, wherein K represents the index of freshness.

2. The method of claim 1, wherein said extract is produced by obtaining a preselected quantity of fish muscle, mixing said preselected quantity of fish muscle with a solution comprising an acid suitable to break the cell membrane of said preselected quantity of said fish muscle and homogenizing said mixture to produce an extract.

3. A method according to claim 2, wherein said solution is a 10% trichloroacetic acid solution.

4. The method of claim 1, wherein said enzyme nucleotidase is immobilized by a crosslinking agent on a polymeric tube.

5. A method according to claim 1, wherein said amperometric probe consists of a platinum anode and a silver/silver chloride cathode, wherein said anode is polarized at +0.5 V to +0.7 V with respect to said cathode.

6. A method according to claim 1, wherein said enzymes xanthine oxidase and nucleoside phosphorylase are co-immobilized on a polymeric membrane, said polymeric membrane being on said probe to form an enzyme electrode.

7. A method according to claim 6, wherein said enzymes are co-immobilized through glutaraldehyde cross-linking with bovine serum albumin and deposited on a nylon 66 membrane having a pore size of about 3 μm.

8. A method according to claim 1, wherein said enzyme nucleotidase is immobilized on a polymeric support.

9. A method according to claim 8, wherein said nucleotidase is immobilized through a glutaraldehyde activation on the wall of a polymeric tube precoated with a thin layer of polyethyleneimine.

10. An enzyme biosensor system for use in the determination of fish freshness from a fish extract obtained by breaking the cell membrane of said fish, the freshness of said fish being determined by monitoring the autolytic degradation of adenosine triphosphate in fish muscles to inosine monophosphate, inosine and hypoxanthine, said system including a biosensor comprising in combination an amperometric probe having thereon a porous membrane having the enzymes xanthine oxidase and nucleoside phosphorylase co-immobilized thereon to form an enzyme electrode and a polymeric support having the enzyme nucleotidase immobilized thereon, a first portion of said extract being contacted with said enzyme electrode to electrochemically measure a value $d_1 = [HxR] + [Hx]$ from the simultaneous determination of the amount of hydrogen peroxide and uric acid resulting from the degradation hypoxanthine and inosine in said first extract portion by said enzyme electrode enzymes wherein [HxR] is the concentration of inosine and [Hx] is the concentration of hypoxanthine, a second portion of said extract being contacted with said enzyme electrode and said polymeric support to electrochemically measure a value $d_2 = [IMP] + [HxR] + [Hx]$ from the simultaneous determination of the amount of hydrogen peroxide and uric acid resulting from the degradation of inosine monophosphate, inosine and hypoxanthine in said second extract portion by said enzyme electrode enzymes and said polymeric support enzyme, wherein [HxR] is the concentration of inosine, [Hx] is the concentration of hypoxanthine and [IMP] is the concentration of inosine monophosphate, whereby the index of freshness is determined from the formula $K = d_1/d_2$, wherein K represents the index of freshness.

11. An enzyme biosensor according to claim 10, wherein said porous membrane is a nylon 66 membrane having a pore size of about 3 μm.

12. An enzyme biosensor according to claim 10, wherein said xanthine oxidase and nucleoside phosphorylase enzymes are co-immobilized through glutaraldehyde cross-linking with bovine serum albumin.

13. An enzyme biosensor system according to claim 10, wherein nucleotidase is immobilized through glutaraldehyde activation on the wall of a polystyrene tube precoated with a thin layer of polyethyleneimine.

14. An enzyme biosensor according to claim 10, wherein said amperometric probe consists of a platinum anode and a silver/silver chloride cathode wherein said anode is polarized at 0.5 V to 0.7 V with respect to said cathode.

* * * * *